United States Patent
Lambert (10) Patent No.: US 6,537,228 B1
(45) Date of Patent: Mar. 25, 2003

(54) APNEA DETECTOR WITH ARTIFACT REJECTION

(75) Inventor: Scott Lambert, East Bethel, MN (US)

(73) Assignee: Cas Medical Systems, Inc., Branford, CT (US)

( * ) Notice: Subject to any disclaimer, the term of this patent is extended or adjusted under 35 U.S.C. 154(b) by 0 days.

(21) Appl. No.: 09/719,868
(22) PCT Filed: Jun. 17, 1999
(86) PCT No.: PCT/US99/13747
§ 371 (c)(1), (2), (4) Date: Apr. 24, 2001
(87) PCT Pub. No.: WO99/65393
PCT Pub. Date: Dec. 23, 1999

Related U.S. Application Data
(60) Provisional application No. 60/089,874, filed on Jun. 19, 1998.

(51) Int. Cl.$^7$ ................................................ A61B 5/02
(52) U.S. Cl. ...................... 600/506; 600/538; 600/547; 128/633; 128/204.23
(58) Field of Search ................................ 600/506, 529, 600/532, 534, 538, 547; 128/633, 204.23

(56) References Cited

U.S. PATENT DOCUMENTS

| 4,449,537 A |   | 5/1984 | Pross et al. |
| 4,802,485 A | * | 2/1989 | Bowers et al. ............... 128/633 |
| 4,803,997 A |   | 2/1989 | Bowman |
| 5,611,349 A |   | 3/1997 | Halleck et al. |
| 5,796,340 A | * | 8/1998 | Miller ........................ 340/573 |
| 6,062,216 A | * | 5/2000 | Corn ....................... 128/204.23 |
| 6,064,910 A | * | 5/2000 | Andersson et al. .......... 607/365 |

FOREIGN PATENT DOCUMENTS

| EP | 0 765 631 | 4/1997 |

* cited by examiner

Primary Examiner—Hieu T. Vo
Assistant Examiner—Johnny H. Hoang
(74) Attorney, Agent, or Firm—Rothwell, Figg, Ernst & Manbeck (57) ABSTRACT

A method and apparatus in an apnea detector monitor impedance pneumographic respiratory signals and heart rate of a patient. Magnitudes of excursions of the respiratory signals are monitored to resolve respiratory events, i.e. breaths, inhalations and exhalations. A counter will reach a threshold count and trigger an alarm if a selected interval lapses without a respiratory event being detected. If a respiratory event is detected, as by detecting successive peaks, a peak or a valley of the respiratory signal, the timer is reset. The method and apparatus reject artifact that would otherwise appear as breathing cycles in order to prevent false negative indications of apnea. Cyclically occurring peaks are rejected as being indicative of a breath if they are in a selected magnitude range compared to that of a normal breath and they approximate the patient's heart rate. Successive peaks due to sighs or of a baseline change are measured for average rate of change over the period it takes for the waveform to decrease from the second peak by a selected level generally corresponding to of a normal inhalation or exhalation. They are rejected as artifact if the change is too slow. Consequently, sighs are not misinterpreted as breaths.

4 Claims, 9 Drawing Sheets

APNEA DETECTOR WITH ARTIFACT REJECTION

This application claims priority from U.S. Provisional Application No. 60/089,874 filed Jun. 19, 1998.

BACKGROUND OF THE INVENTION

1. Field of the Invention

The present invention relates to electronic respiratory monitoring and more particularly to an apnea detection method and apparatus for rejecting artifact and reducing false negative indications of apnea.

2. Description of Related Art

Apnea, from the Greek for "a want of breath," is an interruption in breathing. Apnea or cessation of breathing may be a significant event for people of any age, but is particularly significant in a newborn. Consequences of apnea range from merely annoying to life-threatening. Various prior art schemes have been provided to monitor breathing for the purpose of detecting apnea. Pneumatic systems measure actual air flow. Others measure sounds. A more powerful diagnostic tool has been found in the electronic monitoring of breathing and heartbeat waveforms.

For example, U.S. Pat. No. 5,206,807, issued Apr. 27, 1993 and entitled *Neonatal Cardiorespirograph Incorporating Multi-Variable Display and Memory*, illustrates a system sensors and transducers providing signals indicative of cardiac activity, respiratory effort and relative saturation of oxyhemoglobin and transmits them to a computer. The respiratory effort may be measured by impedance pneumography. The computer produces many outputs including a real time electrocardiogram (ECG) waveform and a display of respiratory effort versus time. These two plots may be combined in a cardiorespirogram (CRG). The system provides a user-settable apnea alarm which is variable from five to 30 second intervals after a last breath. Generally, a delay in breathing over 20 seconds is considered to be an apneic event.

Reliable operation of such a system is dependent upon the pneumograph detecting the absence of a breath. In impedance pneumography for infants, electrodes are placed on an infant chest wall providing a very low current, e.g. 300 $\mu$amps at 40–100 kHz. Volume changes, as for example due to breathing, are accompanied by a change in electrical resistance. A low level signal is produced indicative of chest resistance. If breathing stops and if another low level signal is produced within the delay period following a last breath, a computer may interpret this signal as having been a breath. Causes of such other low level signals include cardiac artifact and change of volume between electrodes not due to breathing activity, such as a sigh. Cardiac artifact may also take the form of high level signals. If such other low level signals are interpreted as a breath, an apneic event will have been missed, and a false negative result provided.

SUMMARY OF THE INVENTION

It is therefore a particular advantage of the present invention to provide a method and apparatus for apnea monitoring utilizing impedance pneumography in which outputs of a respiratory monitor are evaluated for behavior indicative of breathing effort.

It is a further particular advantage of the present invention to provide a method and apparatus of the type described in which cardiac artifact in a respiratory monitor signal output is not detected as respiratory event.

It is a further specific advantage of the present invention that a method and apparatus of the type described are provided in which a respiratory signal possibly indicating a respiratory event is compared to prior and successive corresponding signals for testing for cardiac artifact in the respiratory signal.

Another particular advantage of the present method and apparatus is ability to detect breaths even in view of significant amounts of cardiac artifact.

A further advantage of the present method and apparatus is the ability to resolve potential and actual respiratory events even in the presence of significantly changing or shifting levels of the respiratory signal.

It is a general advantage of the present invention to provide a method and apparatus of the type described in which signals affecting production of an apnea alarm signal are evaluated for preventing false negative results.

A more specific advantage of the present method and apparatus in which rates of changes of respiratory signals are measured so that waveforms possibly indicating a respiratory event are rejected as artifact if their characteristics do not correspond to characteristics of breathing activity.

Briefly stated, in accordance with the present invention, there are provided a method and apparatus in which ECG and electronic respiratory outputs are provided from electrodes on a patient and received for processing. A monitor examines respiratory outputs. The respiratory output, measured by impedance pneumography, will be measured in ohms. A breath begins with an inhalation, represented as a positive amplitude excursion from a minimum to a maximum. An exhalation is represented by a negative amplitude excursion A first level impedance transition is called a "bump." A bump is resolved when a current maximum has been reached and the waveform decreases by at least a first, predetermined amount. Successive bumps may indicate that a breath has occurred. If the time between the current bump, i.e. the time of its maximum, and that of the previous bumps generally corresponds to the period of the heart rate, it may be concluded that the bumps were cardiogenic artifact. If they are not, they are examined to see if the impedance magnitude excursion reaches a second, higher level indicative of the industry standard of a breath. A bump manifesting this second, larger impedance transition level is called a "peak." If the current bump is a peak, it is provisionally recognized as a respiratory event, i.e. a breath. The current bump is then compared to a next bump to again determine whether the current bump and the next bump represent cardiogenic artifact. If not, a breath is detected. Rate of change criteria are used with respect to the respiratory signal to reject waveforms having successive maxima due to a baseline shift or a sigh from being reported as a breath. An alarm may be actuated when a threshold time differential between breaths is exceeded to indicate apnea. The alarm is reset in response to respiratory event. The present invention prevents artifact from forestalling production of an apnea alarm.

BRIEF DESCRIPTION OF THE DRAWINGS

The means and method through which the foregoing advantages and features of invention are achieved are pointed out with particularity in the claims forming the concluding portion of the specification. The invention, both as to its organization and manner of operation may be understood by reference to which the following description taken in connection with the following drawings.

Of the drawings:

FIG. 5, consisting of FIGS. 5a, 5b and 5c, illustrates the method of the present invention for evaluating respiratory signal as respiratory events;

DETAILED DESCRIPTION OF THE PREFERRED EMBODIMENTS

Figure 1:
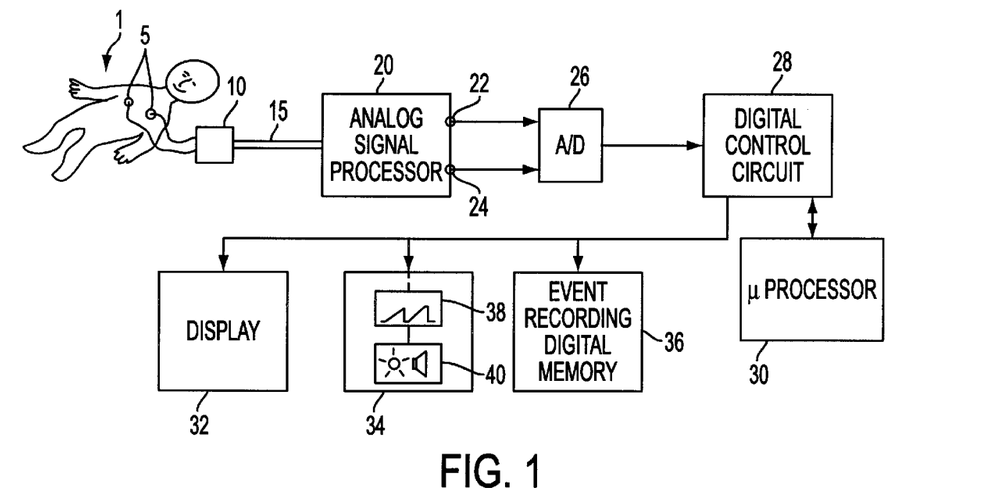
FIG. 1 is a schematic illustration of a patient being monitored by a system constructed in accordance with the present invention.

FIG. 1 is a schematic illustration of a patient 1 being monitored by a system constructed in accordance with the present invention. Electrodes 5 are affixed to the patient 1 in a known manner to provide inputs to an analog monitor circuit 10 which provides a composite respiration and ECG signal. The respiration signal is produced by impedance pneumography. Since the load comprising the patient 1 is substantially non-reactive, impedance in the present specification will be discussed as resistance. The symbol I will be used. A value of I refers to the excursion of I in both the down and up or up and down directions. Units of respiration measurement will be in ohms. The ECG is a conventional magnitude versus time plot. A current heart rate period R is a currently measured R-R interval from one cardiac waveform to a next.

Outputs from the analog monitor circuit 10 are coupled by a cable 15 to an analog processor circuit 20 which resolves the composite respiratory/ECG signal into a respiratory signal at a port 22 and an ECG at a port 24. An analog to digital converter 26 converts the respiratory signal and ECG into digital signals supplied to a control circuit 28 comprising a microprocessor 30. The control circuit 28 controls timing of processing and coupling of signals in a known manner through use of the microprocessor 30. The microprocessor 30 calculates heart rate and detects respiration as described below. The control circuit 28 provides signals to a display 32, an alarm circuit 34 and an event recording digital memory 36.

The alarm circuit 34 functions to measure time interval from a last respiratory event and trigger an alarm when the interval reaches a preselected value. This function may alternatively be done in the processor 30. This value is selected in accordance with the criteria of a particular attending physician or researcher. One embodiment for this function is embodied by an up-counter 38 receiving the respiration signals from the control circuit 28. In a digital embodiment, a periodically updated register would be used in place of an up counter. The up-counter 38 is reset by a current respiratory event signal and begins counting. If a next respiratory event signal is received prior to the end of the preselected interval, the up-counter 38 is reset and does not provide an output. If the respiratory event signal is not received by the end of the interval, the count reaches a threshold level and triggers an alarm driver signal coupled to alarm means 40. The alarm means 40 includes visual and audible alarms and also provides a communications signal to a central nursing desk or other station.

Figure 2:
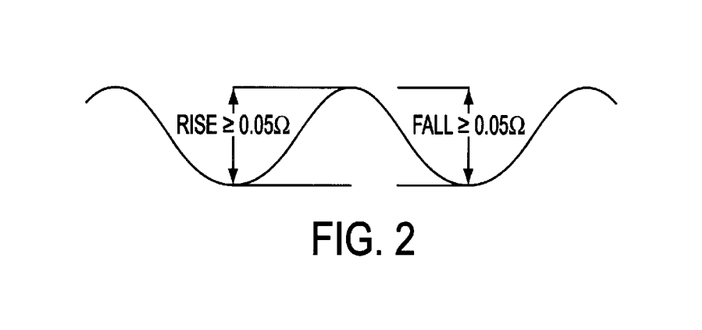
FIGS. 2 and 3 are graphic illustrations of "bumps" and maxima and minima as defined in the present specification.
Figure 3:
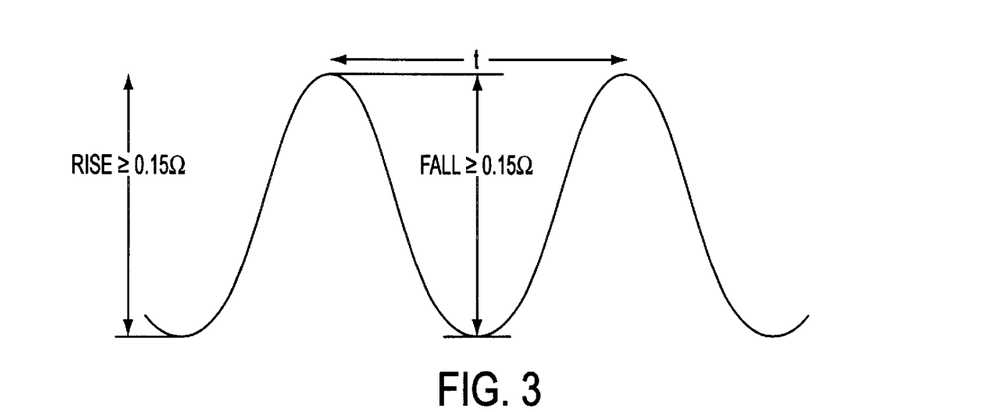

FIGS. 2 and 3 are waveform charts illustrative of respiratory waveform components resolved by the present invention. By examining waveforms comprising the respiratory signal, events can be rejected which do not correspond to respiratory events, whether due to movement or other artifact. In FIGS. 2 and 3, the abscissa is time and the ordinate is ohms. Particular values of the respiratory signal in ohms are discussed below to provide a specific example and to suggest a nominal set of proportions in the signals to be examined. In FIGS. 2 and 3, the maxima and minima of the respiratory waveforms are respectively labeled P to denote inflection points from positive to negative slope and N to denote inflection points from negative to positive slope.

While particular values must be normalized to the particular probes, cables and circuitry used and may even need to be normalized to the patient, there are some recognized Industry norms. It is an industry standard in impedance pneumography to recognize 0.15 Ω as a minimum amplitude excursion indicative of breathing effort. In a nominal situation, the maximum to minimum amplitude excursion for a normal patient could be 1 Ω. In the present invention, a first lower level amplitude excursion is used to resolve bumps as defined immediately below. This value is selected as 0.05 Ω in the present exemplification since this value is significantly below the 0.05 Ω, herein called a second, higher threshold value, and is conveniently processed by current hardware. The 0.05 Ω level is significantly above noise level and easily resolved by currently available hardware.

FIG. 2 illustrates a "bump," i.e. a wave whose rise and whose fall are each $\geq 0.05$ Ω. A peak is a minimum to maximum transition of $\geq 0.15$ Ω. Also, times t are measured. The time t is the distance from maximum to maximum or minimum to minimum in a bump.

Figure 4:
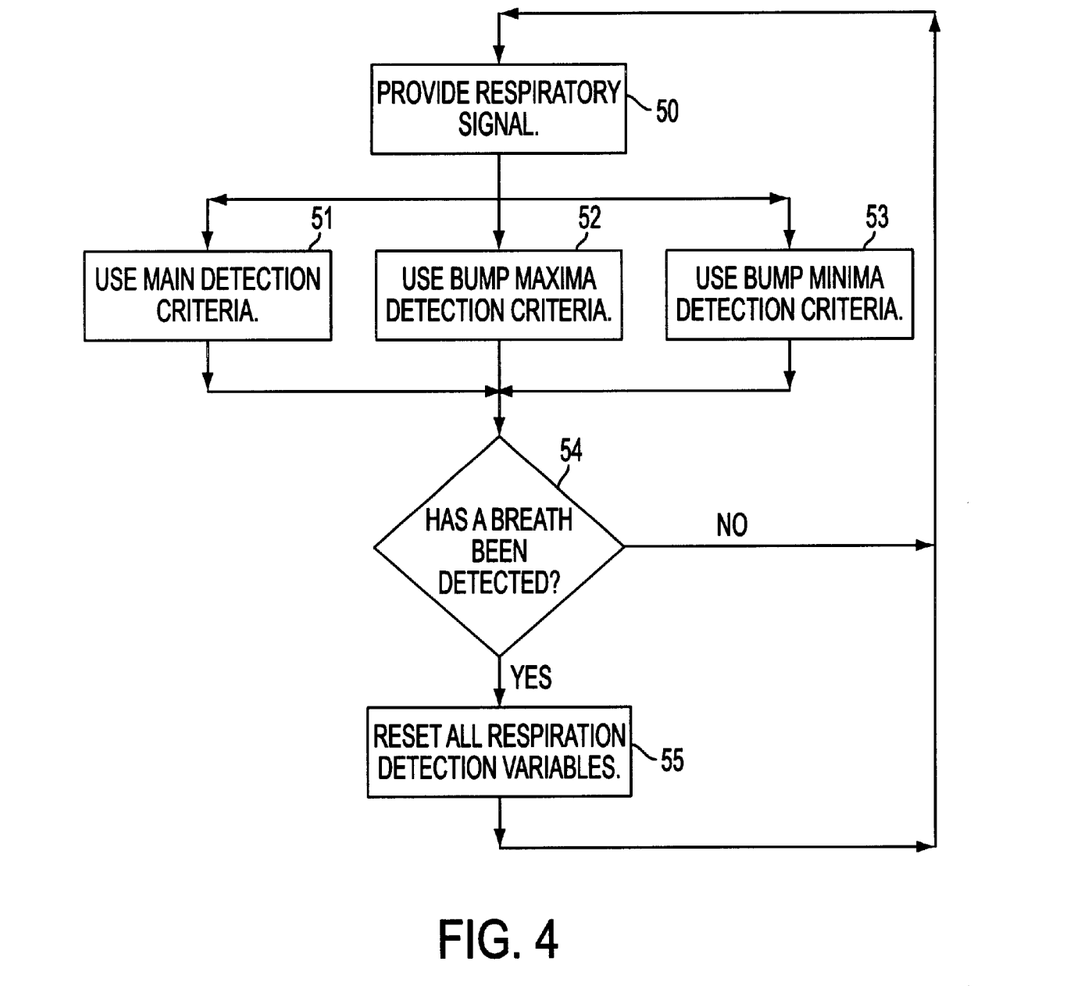
FIG. 4 is a flow chart illustrating an overview of the method of the present invention.

FIGS. 4 and 5 are flow charts illustrating the method of the present invention. The method of the present invention is performed by measuring and evaluating the respiratory signal.

Also, heart rate is measured and used in evaluating selected signals. The following are elements of the method:
Resolve bumps and peaks:
    bump I$\geq$0.05 Ω
    peak I$\geq$0.05 Ω
Resolve forms of cardiogenic artifact (identification of the mechanical motion of the heart that causes impedance changes):

$t=R\pm15\%$

Figure 11:
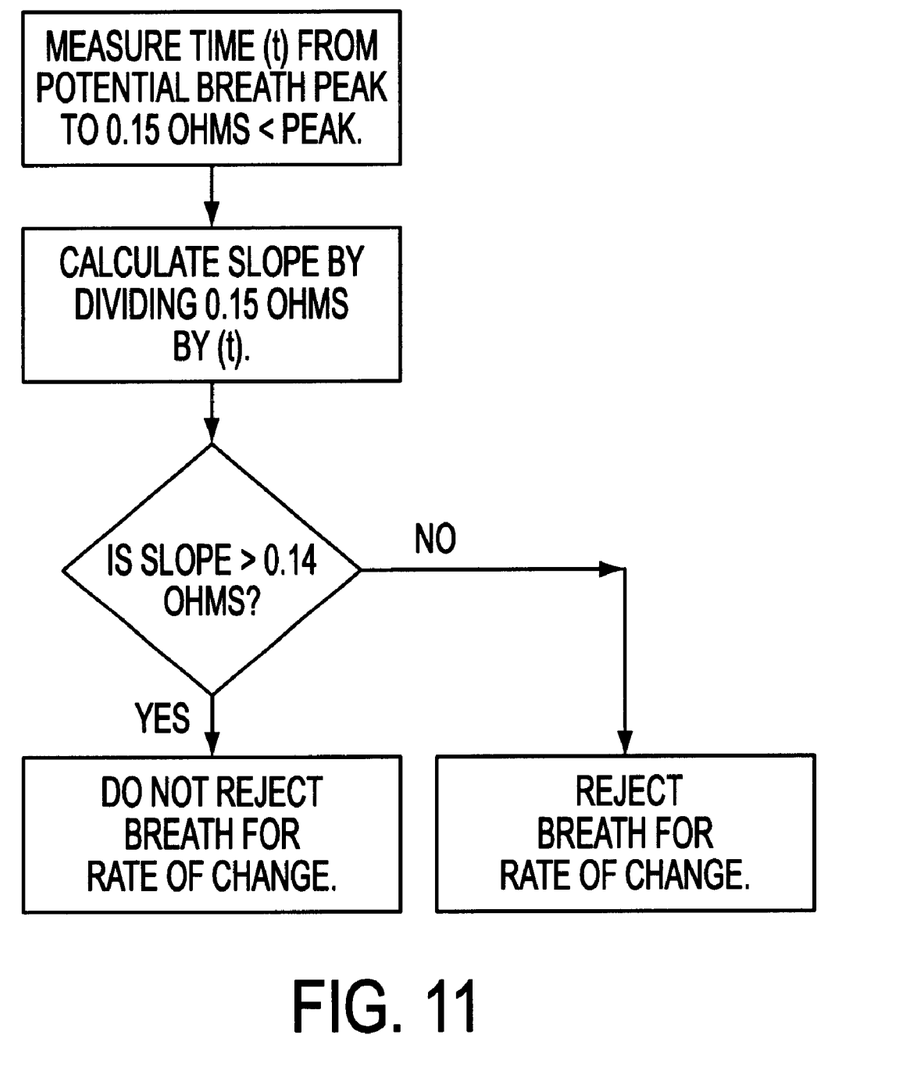
FIGS. 11 and 12 illustrate a method for applying rate of change criterion to possible baseline shift and sigh apnea artifact.
Figure 12:
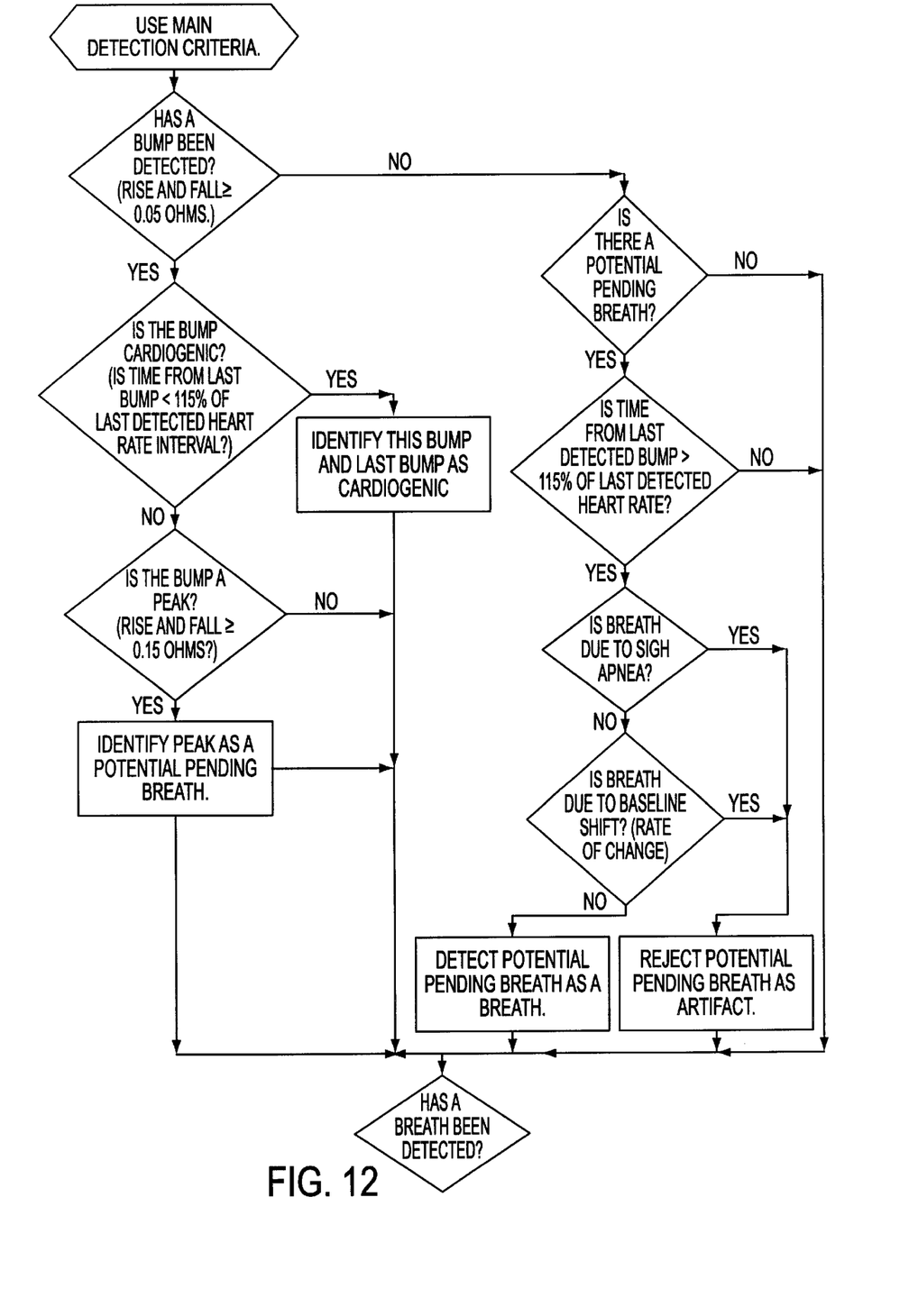

Resolve a breath:
    rise and fall>0.05 Ω and no cardiogenic artifact detected
    cardiogenic bump peaks>0.05 Ω
    cardiogenic bump valleys>0.05 Ω
Reject artifact due to baseline shift:
    after a peak is detected, measure average slope of line from peak to a point 0.05 Ω below peak; reject if slope<0.14 Ω/sec. Performance of this evaluation is illustrated in FIG. 11.
Sigh apnea rejection:
    after a breath peak is detected and t>3 sec. and current peak which is at least 0.05 Ω below prior peak; reject if slope of respiration signal is <0.04 Ω/sec. Performance of this evaluation is illustrated in FIG. 12.
    OR
    if a respiratory peak is detected as a next peak following a peak was a saturated respiration signal and DC restore, i.e. resetting of zero level, was engaged, reject if slope<0.04 Ω/sec.

The sigh apnea rejection criteria are applied to all respiratory input signals. After the sigh apnea rejection criteria are applied, the system utilizes the 0.14 Ω/sec. slope criterion to judge whether a potential breath is related to motion. Once a respiratory event is detected, the counter 38 (FIG. 1) is disabled and an apnea alarm is prevented. The present invention prevents artifact from preventing an alarm.

Figure 5A:
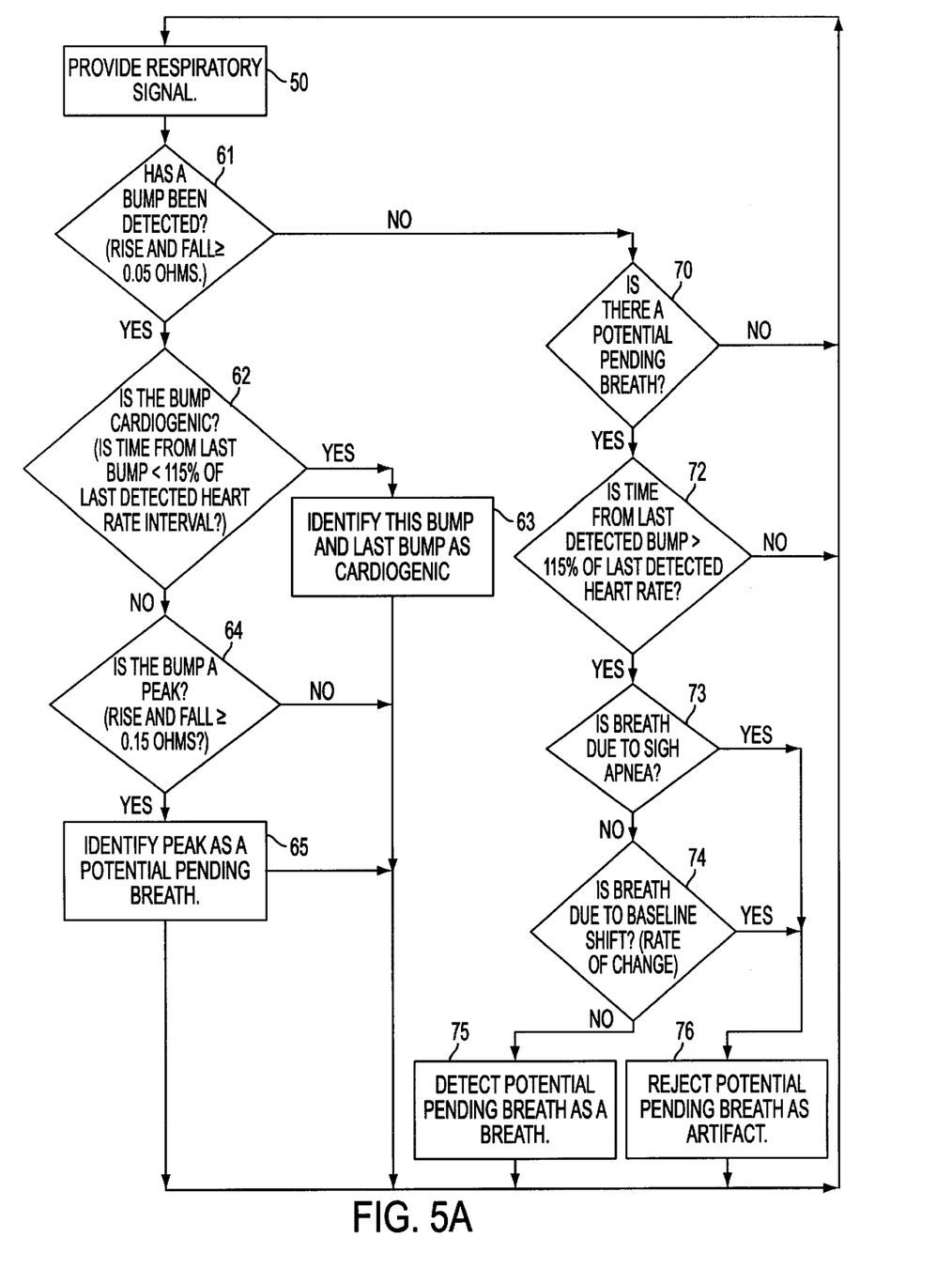
Figure 5B:
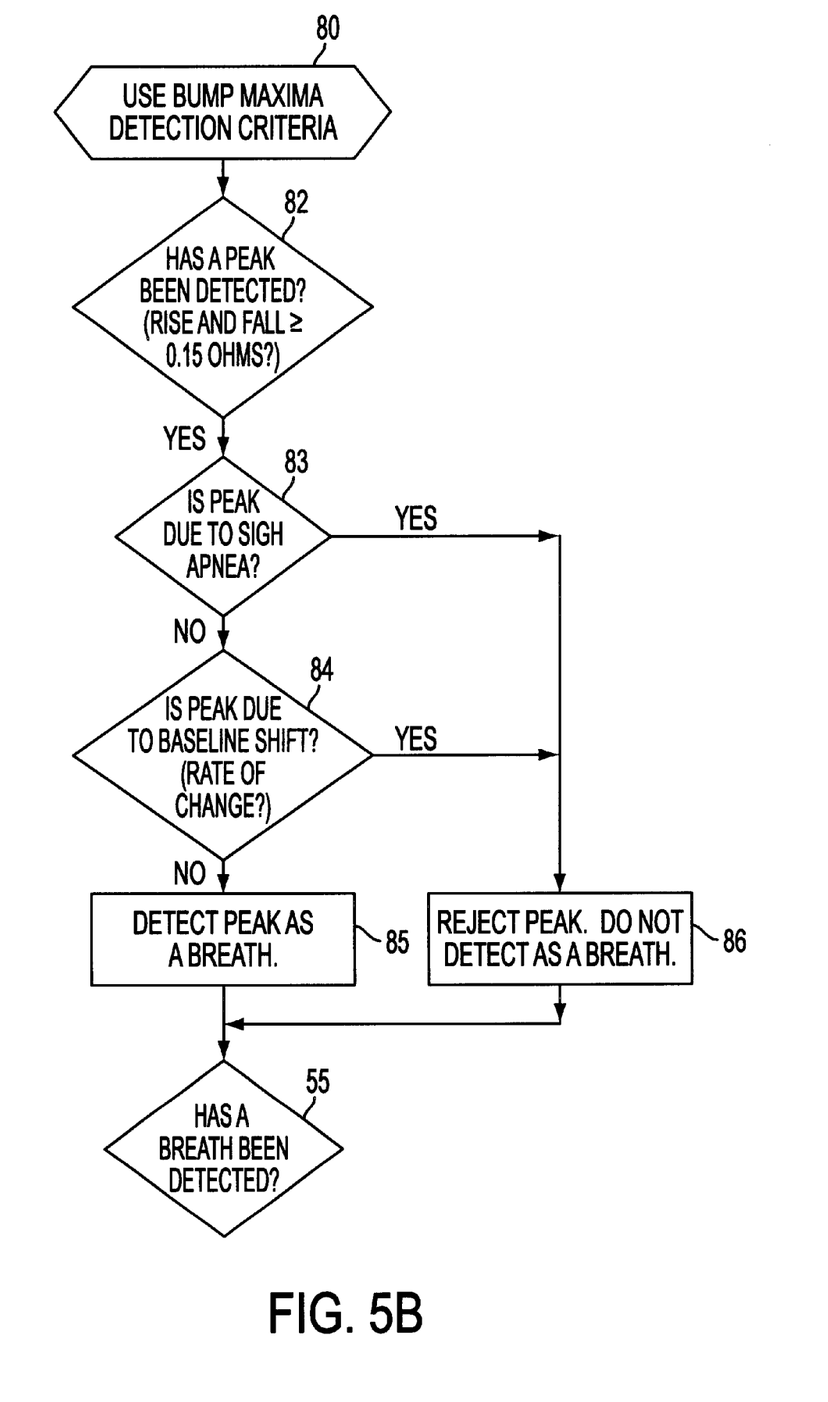
Figure 5C:
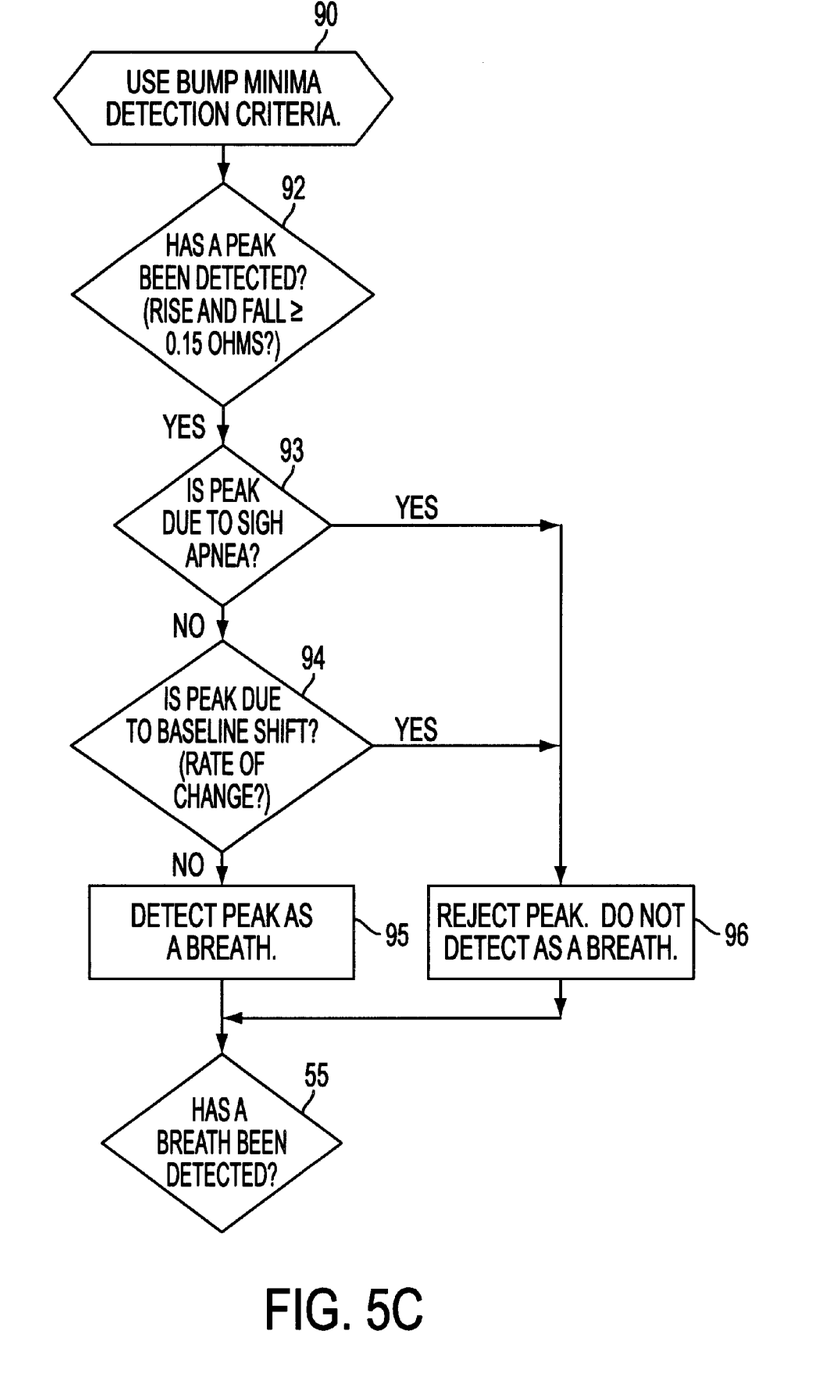

FIG. 4 is a flow chart illustrating an overview of the method of the present invention and FIG. 5, consisting of FIGS. 5a, 5b and 5c, illustrates the method of the present invention. Generally stated, a bump is resolved when a current maximum has been reached and the waveform decreases by at least a first, predetermined amount. Successive bumps may indicate that a breath has occurred. If the time between the current bump, i.e. the time of its maximum, and that of the previous bumps generally corresponds to the period of the heart rate, it may be concluded that the bumps were cardiogenic artifact. It they are not, they are examined to see if the impedance magnitude excursion reaches a second, higher level indicative of the industry standard of a breath. A bump manifesting this second, larger impedance transition level is called a "peak." If the current bump is a peak, it is provisionally recognized as a respiratory event, i.e. a breath. The current bump is then compared to a next bump to again determine whether the current bump and the next bump represent cardiogenic artifact. If not, a breath is detected. Rate of change criteria are used with respect to the respiratory signal to reject waveforms having successive maxima due to a baseline shift or a sigh from being reported as a breath. Three maxima of the respiratory waveform must be examined. FIG. 5a illustrates the main detection method of resolving a bump and determining if it is representative of cardiac artifact. FIG. 5b illustrates evaluation of maxima waveforms for presence of a "peak," and FIG. 5c represents evaluation of minima waveforms for presence of a "peak." Maxima and minima waveforms are the envelopes respectively of positive inflection points P and negative inflection points N as further described with respect to FIG. 7. These waveforms include cardiac artifact modulated thereon.

In FIG. 4, box 50 indicates the step of providing a respiratory signal for examination. At boxes 51, 52 and 53 the steps of applying criteria for bumps, maxima and minima are performed. Then it is seen, at box 54 if a breath has been detected. If not, the system waits for another signal to analyze. If so, as at box 55, all detection variables are reset. Detection variables include stored indications of a current or previous bump as further described below.

Referring now to FIG. 5a, at box 61, the respiratory waveform provided in the step at box 50 is compared to bump criteria. If a bump is detected, it must be compared to a prior bump, box 62. For purposes of the present description, the current bump will be regarded as a bump occurring at time t2 and the previous bump occurred at time t1. In this step, t2−t1 is compared to the period R of the heart rate, and if the interval t2−t1>1.15 R, both the bumps at t1 and t2 are identified as cardiogenic, box 63. The next step is to return to look at the respiratory signal for resolving a next bump. If the bump is not cardiogenic, it is compared to the 0.15 Ω second threshold level as seen in box 64. If the bump is not a peak, the system awaits a next bump. If the bump is a peak, the peak is identified as a potential pending breath in the step at box 65.

Also, as seen in the step at box 70, even when there is no new bump to process, it is necessary to see if there was a bump recognized that was recognized as a potential breath at time t2 that must be compared to a bump at time t3. If not, box 50 is returned to. If so, a comparison indicated at box 72 is performed to determine if the interval between bumps at t2 and t3 represent a potential breath rather than cardiac artifact. If so the sigh apnea comparison according to the above-stated standards is performed as seen at box 73. If a potential breath is indicated, then the comparison to the baseline shift criteria stated above is performed at box 74. If the baseline shift or sigh criteria are met and artifact is indicated, then the step at box 75 of rejecting the potential pending breath as artifact is performed. If the potential pending breath is not due to baseline shift, breath is detected.

FIG. 5b represents details of box 52 and FIG. 5c illustrates the details of box 53. The maxima and the minima respiratory input signals are the envelope of cardiogenic waveform inflection points. Bump data is resolved in FIG. 5b at box 80 and in FIG. 5c at box 90, and the process corresponding to that at boxes 72–76 is performed to resolve a respiratory event.

Figure 6:
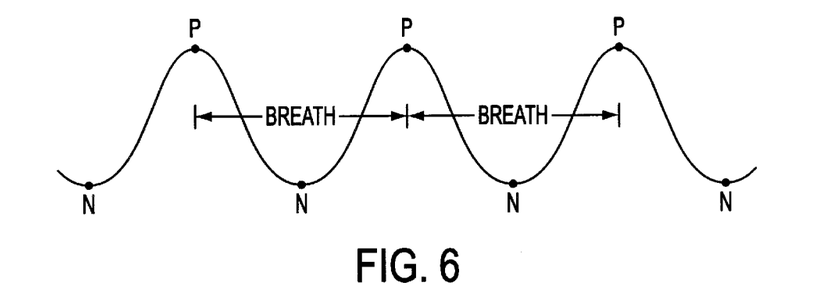
FIGS. 6–10 are waveform charts illustrating operation of the present invention under varying circumstances.
Figure 7:
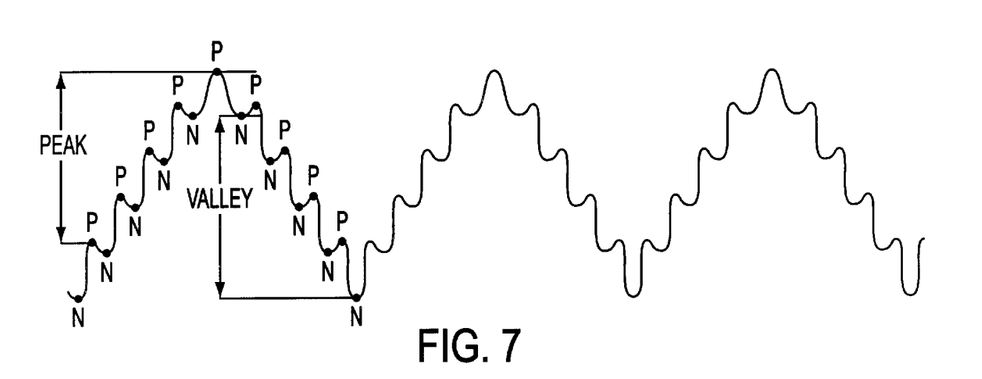

Operation of the present invention is further described with respect to FIGS. 6–10, which are each a waveform chart of arbitrary dimension illustrating a different scenario in operation. Again, the abscissa is time and the ordinate is impedance. FIGS. 6 and 7 represent respectively a respiratory signal indicative of generally normal breathing without and with cardiogenic artifact. Dots on the waveform in FIG. 6 indicates peaks and valleys as defined above.

In FIG. 7, the maxima and minima of the cardiac artifact modulated on the respiratory waveform are respectively labeled P to denote inflection points from positive to negative slope and N to denote inflection points from negative to positive slope. Maxima are measured in the scenario of FIG. 7 on the envelope of the P inflection points and minima are measured on the envelope of the N inflection points. It is noted that a nominal heart rate R is higher than a nominal breathing rate 1/t. Therefore, the comparison of time between successive maxima to t is a very useful tool.

Figure 8:
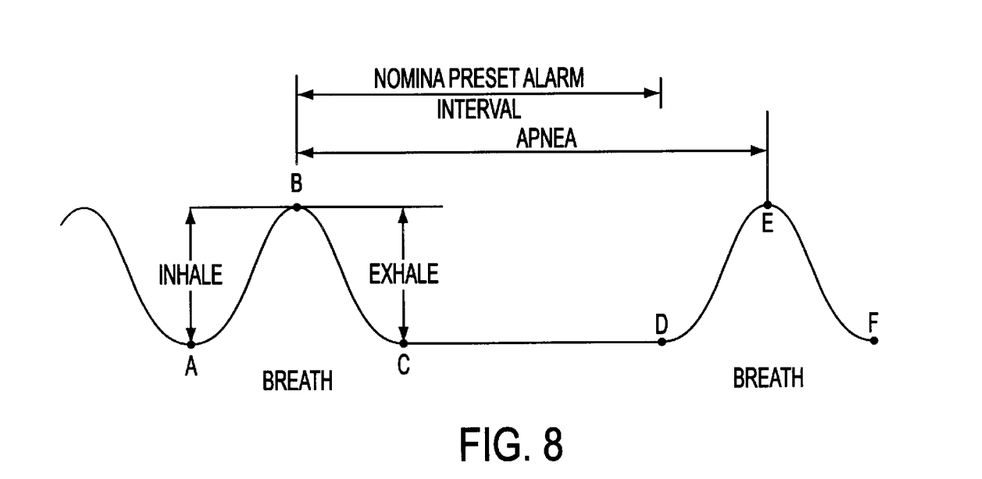

FIG. 8 illustrates apnea. Inhalation and exhalation are represented as positive and negative transition. In the present illustration, inhalation is shown between points A and B on the respiratory signal curve; exhalation for point B to point C. A–C comprises respiratory event, i.e. a breath. When apnea occurs, breathing ceases. The respiratory signal remains flat for a long time compared to a "close to zero" value around an inflection point in a breath. In the present illustration, a next breath does not begin until point D, increasing to point E, and exhalation is completed at point F. One value of the preselected interval is illustrated in the time dimension.

Figure 9:
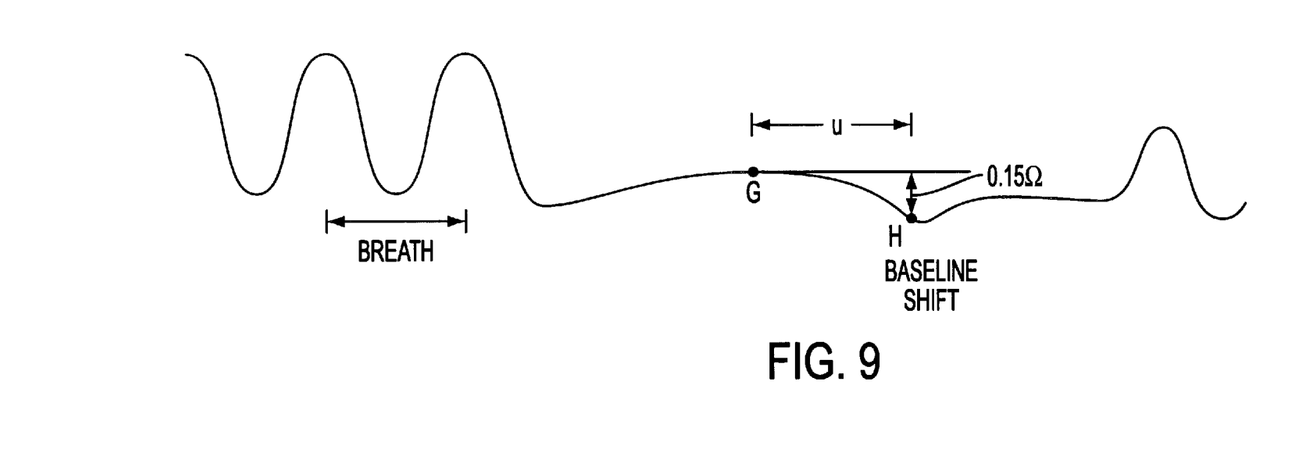

FIG. 9 represents apnea with a baseline shift. Breaths are indicated as the normal sinusoidal wave of the respiration signal. A baseline shift, such as a compression of the body due to movements causes an increase, decrease and increase in the value I. In this particular example, the transition from maximum to minimum occurs over a time u. The slope is measured of the line through maximum point G and a point H. The point H is the point on the respiratory signal waveform 0.15 Ω below point G. If 0.15 Ω/u<0.14 Ω/sec., where u is the time interval between point G and point H, the waveform is not seen to behave as a breath, but rather as artifact. The counter 38 (FIG. 1) will not be reset, and a false negative indication of apnea will be prevented.

Figure 10:
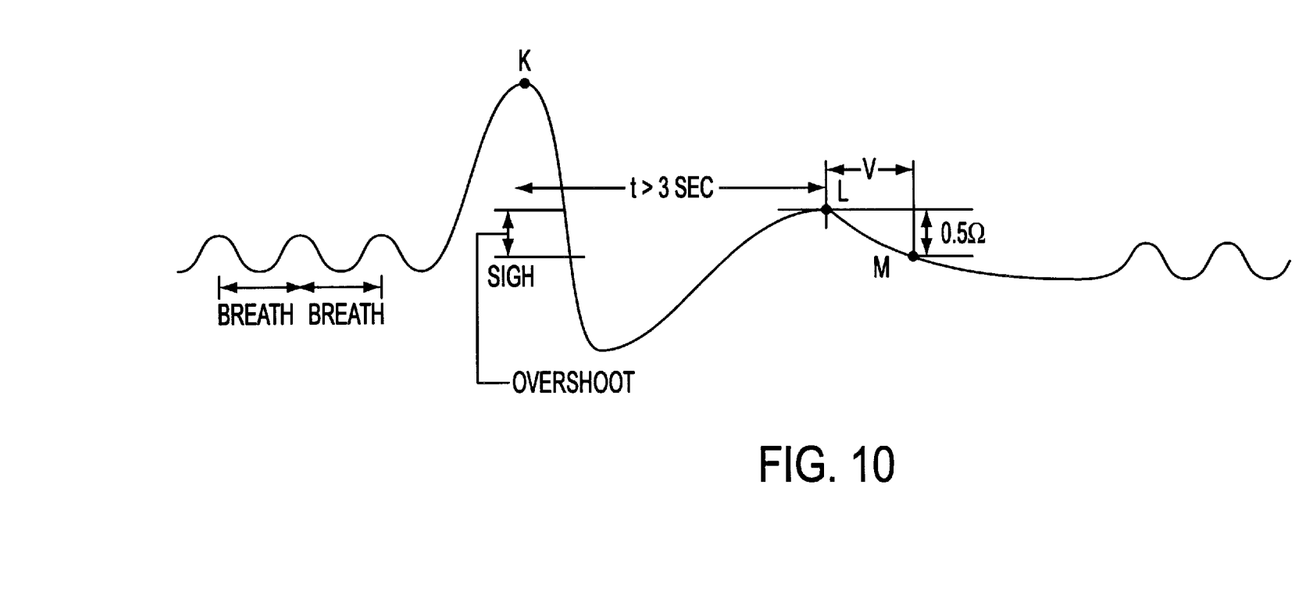

FIG. 10 represents the wave resolved and analyzed by the process initiated at box 73 in FIG. 5a. After normal breaths, a sigh takes place. Sighs are expulsions of air, but do not need to be caused by breathing. In the present example, there is a large exhalation beginning at point K, which saturates the sensor circuitry such as 10 and 20 in FIG. 1. An overshoot in the respiratory signal occurs which results in a P inflection point on the waveform at point L as the waveform settles. By sensing temporal distance of point K to point L, e.g. greater than three seconds, the possibility of point L being part of an overshoot waveform is recognized. Point L must also be at least 0.5 Ω lower than point K. The slope is measured of the line through inflection point L and a point M. The point M is the point on the respiratory signal waveform 0.5 Ω below point L. If 0.5 Ω/v <0.14 Ω/sec., where v is the time interval between point L and point M, the waveform is not seen to behave as a breath, but rather as the result of an overshoot. The counter 38 (FIG. 1) will not be reset, and a false negative indication of apnea will be prevented.

Of course, the present specification will enable those skilled in the art to produce many different forms monitor not specifically illustrated above that are in accordance with the present invention.

What is claimed is:

1. An apnea monitor comprising:
   a signal processor which receives an impedance pneumography signal and a heart rate signal from a patient and measures an amplitude excursion between a first inflection point and a second inflection point of said impedance pneumography signal;
   a threshold detector which classifies said excursion as a first type if it exceeds a first, lower threshold or as a second type if it exceeds a second, higher threshold and discards said excursion if it is below said first threshold;
   a timer which measures a time interval from said first inflection point to said second inflection point;
   a comparator which compares said time interval to a period of said heart rate signal; and
   a discriminator which rejects said first and second inflection points when the time interval is within a preselected range; and
   an identifier which identifies said second inflection point as a respiratory event if said time interval is outside of said preselected range or said excursion is of said second type.

2. The monitor according to claim 1 comprising further a processor which compares a rate of change of said impedance pneumography signal with a preselected rate of change indicative of breathing effort; and
   a reporting device which reports said excursion as an artifact when the rate of change is below the preselected rate of change.

3. A method for evaluating respiration comprising the steps of:
   a) providing a heart rate signal and an impedance pneumography signal based on electronic ECG and respiratory outputs from electrodes on a patient;
   b) detecting a first and second inflection points in said impedance pneumography signal;
   c) determining a time interval between said first inflection point and said second inflection point;
   d) rejecting said first and second inflection points if the time interval is less than or substantially equal to a period of the heart rate signal;
   e) comparing an excursion between said first and second inflection points with a first lower level and rejecting said first and second inflection points if the excursion is less than said first lower level; and
   f) comparing said excursion to a second, higher level indicative of a breath and reporting a respiratory event if the excursion exceeds the second, higher level.

4. The method of claim 3 further comprising the steps of:
   determining a rate of change of said impedance pneumography signal for which said respiratory event has been reported; and
   determining if said rate of change is indicative of baseline shift or sigh apnea.

* * * * *